(12) United States Patent
Kayukawa et al.

(10) Patent No.: US 11,744,533 B2
(45) Date of Patent: Sep. 5, 2023

(54) X-RAY DIAGNOSTIC APPARATUS AND SCATTERED-RAY REMOVING DEVICE

(71) Applicant: CANON MEDICAL SYSTEMS CORPORATION, Otawara (JP)

(72) Inventors: Yosuke Kayukawa, Otawara (JP); Mitsunobu Sugeno, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 77 days.

(21) Appl. No.: 17/136,096

(22) Filed: Dec. 29, 2020

(65) Prior Publication Data

US 2021/0236074 A1    Aug. 5, 2021

(30) Foreign Application Priority Data

Jan. 30, 2020    (JP) .................................. 2020-013903

(51) Int. Cl.
    *A61B 6/00*    (2006.01)
(52) U.S. Cl.
    CPC .................................. *A61B 6/4291* (2013.01)
(58) Field of Classification Search
    CPC .................................................. A61B 6/4291
    See application file for complete search history.

(56) References Cited

U.S. PATENT DOCUMENTS

| | | | | |
|---|---|---|---|---|
| 4,063,100 A * | 12/1977 | Williams | .................. | A61B 6/06 378/177 |
| 4,132,897 A * | 1/1979 | Ohlson | ................ | G03B 42/025 378/154 |
| 4,310,766 A * | 1/1982 | Finkenzeller | ........ | G03B 42/025 378/155 |
| 4,429,412 A * | 1/1984 | Pierce | .................. | G03B 42/047 378/182 |
| 4,914,685 A * | 4/1990 | Yanome | .................... | G21K 1/10 378/154 |
| 5,809,107 A * | 9/1998 | Schmitt | .................. | G03B 42/02 378/186 |
| 8,891,735 B2 * | 11/2014 | Li | .......................... | A61B 6/583 378/155 |
| 2008/0159486 A1 * | 7/2008 | Hesl | ..................... | A61B 6/4464 378/189 |
| 2008/0165931 A1 * | 7/2008 | Luusua | ................ | A61B 6/4405 378/154 |

(Continued)

FOREIGN PATENT DOCUMENTS

| | | | |
|---|---|---|---|
| JP | 2000-126167 A | 5/2000 |
| JP | 2001-333895 A | 12/2001 |

(Continued)

*Primary Examiner* — Blake C Riddick
(74) *Attorney, Agent, or Firm* — Oblon, McClelland, Maier & Neustadt, L.L.P.

(57) ABSTRACT

An X-ray diagnostic apparatus according to an embodiment includes an X-ray generator configured to generate X-rays, a grid configured to remove scattered rays from the X-rays emitted from the X-ray generator, an X-ray detector configured to detect the X-rays that have passed through the grid, a first support configured to support the grid, and a second support configured to support the grid. The number of directions in which the first support restricts movement of the grid is different from the number of directions in which the second support restricts movement of the grid.

14 Claims, 11 Drawing Sheets

(56) References Cited

U.S. PATENT DOCUMENTS

| | | | | |
|---|---|---|---|---|
| 2012/0217395 A1* | 8/2012 | Kobayashi | ............ | A61B 6/4233 |
| | | | | 250/336.1 |
| 2015/0243398 A1* | 8/2015 | Nam | ........................ | G21K 5/08 |
| | | | | 250/336.1 |
| 2015/0359495 A1* | 12/2015 | Lee | ........................ | A61B 6/502 |
| | | | | 378/155 |

FOREIGN PATENT DOCUMENTS

| | | |
|---|---|---|
| JP | 2003-185755 A | 7/2003 |
| JP | 2017-18434 A | 1/2017 |

\* cited by examiner

| GRID STATE | BALL PLUNGER 52 | BALL PLUNGER 51 | BALL PLUNGER 54 | BALL PLUNGER 53 |
|---|---|---|---|---|
| ATTACHED STATE | ON | ON | ON (I) | ON |
| DETACHED STATE | OFF | OFF | OFF | OFF |
| ALMOST DETACHED STATE | ON | ON | ON (II) | ON |
| | ON | OFF | ON (II) | ON |
| | ON | ON | ON (II) | OFF |
| | ON | OFF | ON (II) | OFF |

X-RAY DIAGNOSTIC APPARATUS AND SCATTERED-RAY REMOVING DEVICE

CROSS-REFERENCE TO RELATED APPLICATIONS

This application is based upon and claims the benefit of priority from Japanese Patent Application No. 2020-013903, filed on Jan. 30, 2020; the entire contents of which are incorporated herein by reference.

FIELD

Embodiments disclosed in the present specification and the drawings relate to an x-ray diagnostic apparatus and a scattered-ray removing device.

BACKGROUND

In an X-ray diagnostic apparatus, the image quality of an X-ray image may be deteriorated because of x-rays scattered by a site in a subject or so called scattered rays. In this case, a grid for removing the scattered rays is attached to an X-ray detector. On the other hand, in a case where it is necessary to prevent increase of the X-ray dose, for example, in pediatric imaging, the grid is detached from the X-ray detector. Therefore, the X-ray diagnostic apparatus is provided with a mechanism for attaching and detaching the grid to and from the X-ray detector.

DETAILED DESCRIPTION

A conventional attaching/detaching mechanism for a grid requires provision of a small gap in order to allow the grid to be detached therefrom while the grid is fixed to an X-ray detector. Insufficient dimension accuracy of this gap causes deterioration of the image quality of an X-ray image due to misalignment, rattle, or the like of the grid, and therefore the conventional attaching/detaching mechanism is required to have high processing accuracy.

One of problems to be solved by embodiments disclosed in the present specification and the drawings is to enable a grid to be attached and detached without being constrained by high processing accuracy. However, the problems to be solved by the embodiments disclosed in the present specification and the drawings are not limited to the above described problems. Problems to be resolved by each of effects by respective configurations in the embodiments described below may be also regarded as other problems.

An X-ray diagnostic apparatus according to an embodiment includes an X-ray generator configured to generate X-rays, a grid configured to remove scattered rays from the X-rays emitted from the X-ray generator, an X-ray detector configured to detect the X-rays that have passed through the grid, a first support configured to support the grid, and a second support configured to support the grid. The number of directions in which the first support restricts movement of the grid is different from the number of directions in which the second support restricts movement of the grid.

Embodiments will be described below with reference to the drawings. The embodiments do not limit the present invention. In the following descriptions, constituent elements having substantially the same functions and configurations are denoted by like reference signs, and redundant explanations thereof will be made only as needed.

First Embodiment

Figure 1:
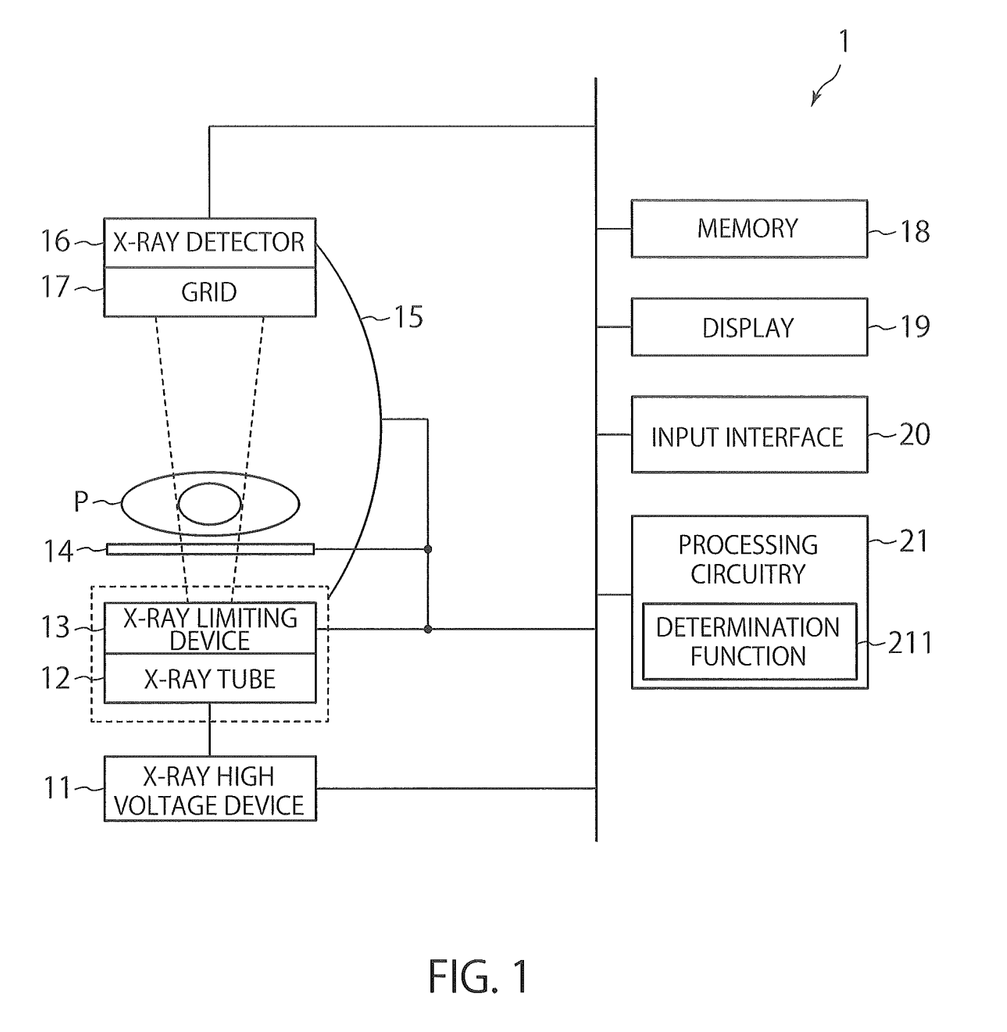
FIG. 1 is a diagram illustrating a schematic configuration of an X-ray diagnostic apparatus according to a first embodiment.

FIG. 1 is a diagram illustrating a schematic configuration of an X-ray diagnostic apparatus according to a first embodiment. An X-ray diagnostic apparatus 1 illustrated in FIG. 1 includes an X-ray high voltage device 11, an X-ray tube 12, an X-ray limiting device 13, a bed device 14, a rotating frame 15, an X-ray detector 16, a grid, 17, a memory 18, a display 19, an input interface 20, and a processing circuitry 21.

The X-ray high voltage device 11 includes a high voltage generator that includes electric circuits, for example, a transformer and a rectifier and has a function of generating a high voltage to be applied to the X-ray tube 12, and an X-ray controller that controls an output voltage in accordance with X-rays radiated from the X-ray tube 12.

The X-ray tube 12 is a vacuum tube that radiates thermions from a cathode (a filament) to an anode (a target) to generate X-rays by application of a high voltage from the X-ray high voltage device 11. The X-ray tube 12 is an example of an X-ray generator.

The X-ray limiting device 13 is, for example, lead plates for limiting the radiation range of the X-rays emitted from the X-ray tube 12. In the X-ray limiting device 13, a plurality of lead plates or the like are combined with each other to form a slit.

A subject P that is an object of examination is placed on the bed device 14. Further, the bed device 14 moves this subject P to the rotating frame 15.

The rotating frame 15 is a ring-shaped frame that rotates the X-ray tube 12 and the X-ray detector 16 when the subject P placed on the bed device 14 is subjected to X-ray examination.

The X-ray detector 16 detects X-rays that have been radiated from the X-ray tube 12 and have passed through the subject P. Further, the X-ray detector 16 outputs an electric signal corresponding to the detected X-ray dose.

The grid 17 removes scattered rays from the X-rays emitted from the X-ray tube 12. The scattered rays are X-rays scattered by a site in the subject P. In order to prevent detection of the scattered rays by the X-ray detector 16, the grid 17 is attached to the X-ray detector 16 on an X-ray incident surface side (a front surface side). The grid 17 is a flat plate member having a surface with lead foil attached thereto, for example. Further, the grid 17 is attached to the X-ray detector 16 in a detachable manner by an attaching/detaching mechanism described later. The grid 17 and the attaching/detaching mechanism described later configure a scattered-ray removing device that is a portion of the X-ray diagnostic apparatus 1.

The memory 18 stores therein various types of data, for example, an X-ray image.

The display 19 displays various types of information. For example, the display 19 outputs a GUI (Graphical User Interface) for accepting the above-described image data, various types of operations from an operator, or the like.

The input interface 20 accepts input from the operator.

The processing circuitry 21 is a processor that controls an operation of the overall X-ray diagnostic apparatus 1. Further, the processing circuitry 21 has a determination function 211. The determination function 211 determines the state of attachment of the grid 17 to the X-ray detector 16 based on the state of the attaching/detaching mechanism described later. The processing circuitry 21 implements the determination function 211 by reading out a program corresponding to the determination function 211 from the memory 18 and executing the program.

While an example in which a "processor" reads out a program corresponding to each function from a storage circuit and executes the program has been described in the above description, the embodiment is not limited thereto. The term "processor" represents a circuit such as a CPU (Central Processing Unit), a GPU (Graphics Processing Unit), an ASIC (Application Specific Integrated Circuit), a Programmable Logic Device (such as an SPLD (Simple Programmable Logic Device)), a CPLD (Complex Programmable Logic Device), and an FPGA (Field Programmable Gate Array). When the processor is a CPU, for example, the processor implements the function by reading out a program stored in the storage circuit and executing the program. Meanwhile, when the processor is an ASIC, instead of storing the program in the storage circuit, the corresponding function is directly incorporated in the circuit of the processor as a logic circuit.

Next, an attaching/detaching mechanism for attaching and detaching the grid 17 to and from the X-ray detector 16 is described. First, the structure of the attaching/detaching mechanism on the grid 17 side is described.

Figure 2A:
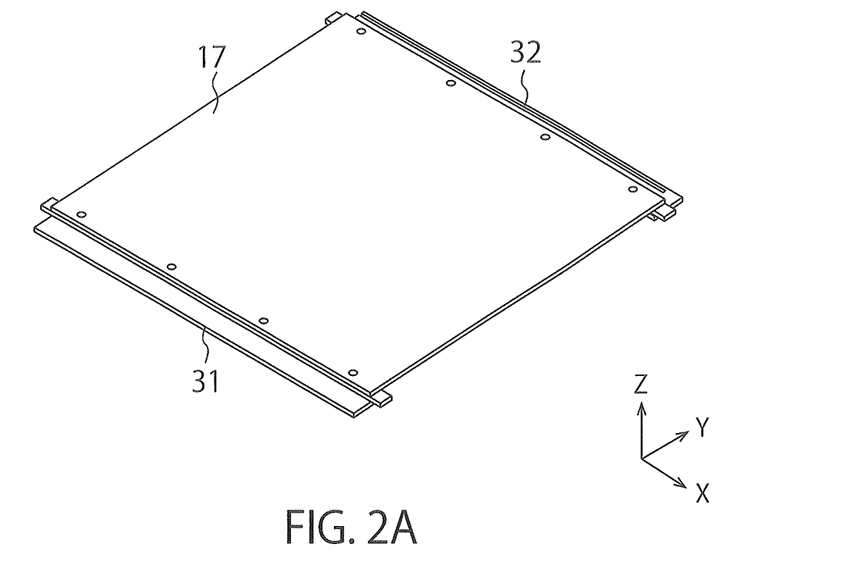
FIG. 2A is a perspective view of an attaching/detaching mechanism as viewed from a top surface of a grid.
Figure 2B:
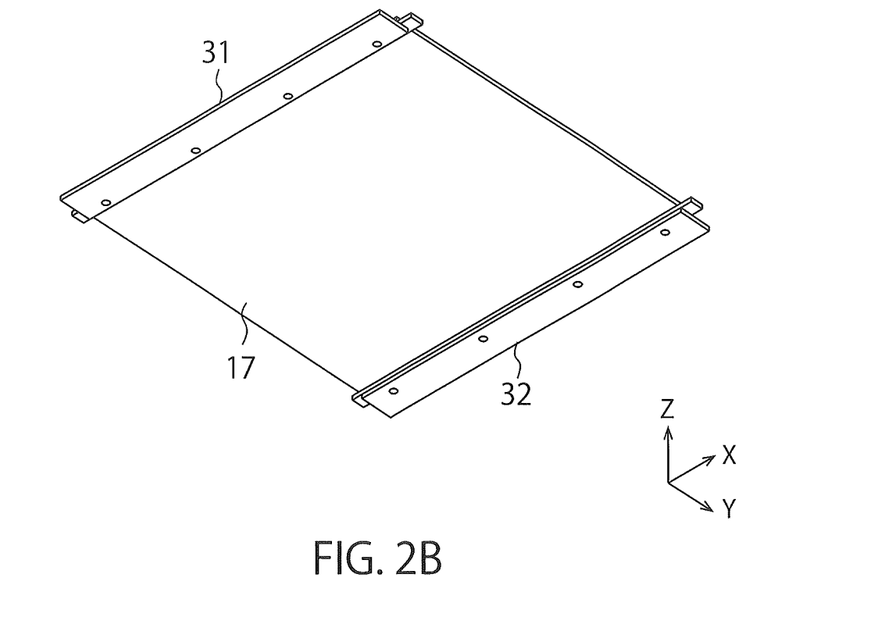
FIG. 2B is a perspective view of the attaching/detaching mechanism as viewed from a bottom surface of the grid.

FIG. 2A is a perspective view of the attaching/detaching mechanism as viewed from a top surface (a surface opposed to the X-ray detector 16) of the grid 17. FIG. 2B is a perspective view of the attaching/detaching mechanism as viewed from a bottom surface of the grid 17.

A Z-direction (a first direction) in FIGS. 2A and 2B is a direction perpendicular to the grid 17. A X-direction (a second direction) is a direction orthogonal to the Z-direction and a direction in which the grid 17 is attached and detached. A Y-direction (a third direction) is a direction orthogonal to the X-direction and the Z-direction. These directions are defined also in other drawings in a similar manner.

As illustrated in FIGS. 2A and 2B, a first rail 31 is fixed to one end of the grid 17 which extends in the X-direction, and a second rail 32 is fixed to the other end of the grid 17 which is opposed to the one end in the Y-direction. In other words, the first rail 31 and the second rail 32 are fixed to both end portions of the grid 17 to be opposed to each other in the Y-direction.

Figure 3A:
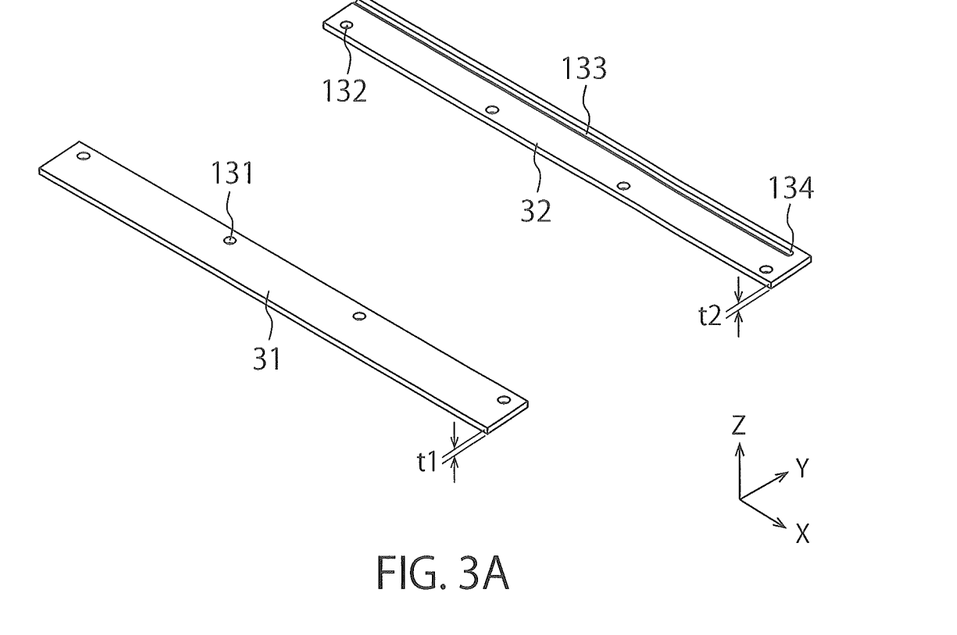
FIG. 3A is a perspective view of a first rail and a second rail.
Figure 3B:
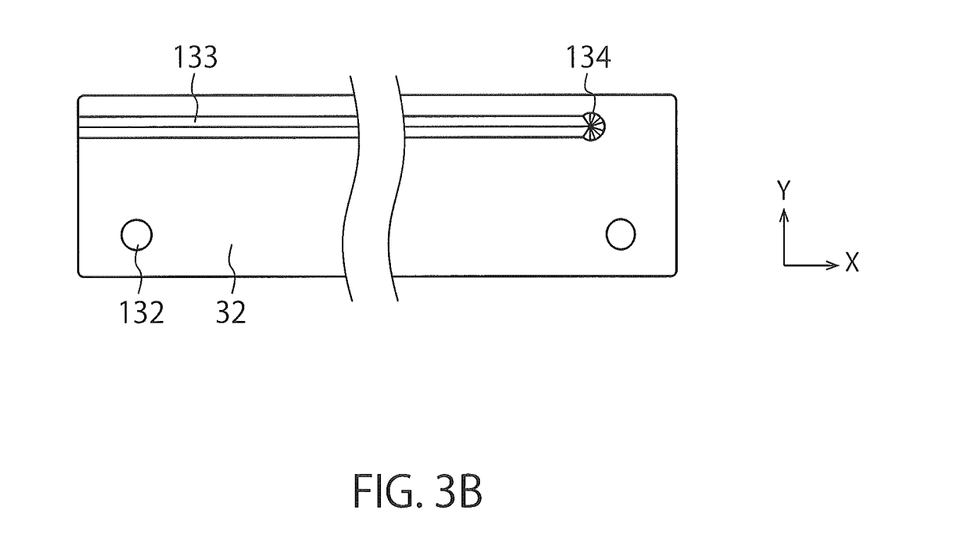
FIG. 3B is an enlarged plan view of a portion of the second rail.

FIG. 3A is a perspective view of the first rail 31 and the second rail 32. FIG. 3B is an enlarged plan view of a portion of the second rail 32. The first rail 31 and the second rail 32 are flat plate members that configure an attaching/detaching mechanism provided on the grid 17 side. In order to avoid misattachment of the grid 17 to the X-ray detector 16, a thickness t1 of the first rail 31 may be different from a thickness t2 of the second rail 32.

A through hole 131 for screwing the grid 17 is formed in the first rail 31. Similarly, a through hole 132 is formed in the second rail 32. Further, a top surface of the first rail 31 is entirely a flat region. Meanwhile, in a top surface of the second rail 32, a V-shaped groove 133 extending in the X-direction and a centering hole 134 adjacent to an end of the groove 133 in the X-direction are formed, as illustrated in FIG. 3B. The centering hole 134 is an example of a concave portion for fixing the grid 17.

Next, the structure of the attaching/detaching mechanism on the X-ray detector 16 side is described.

Figure 4A:
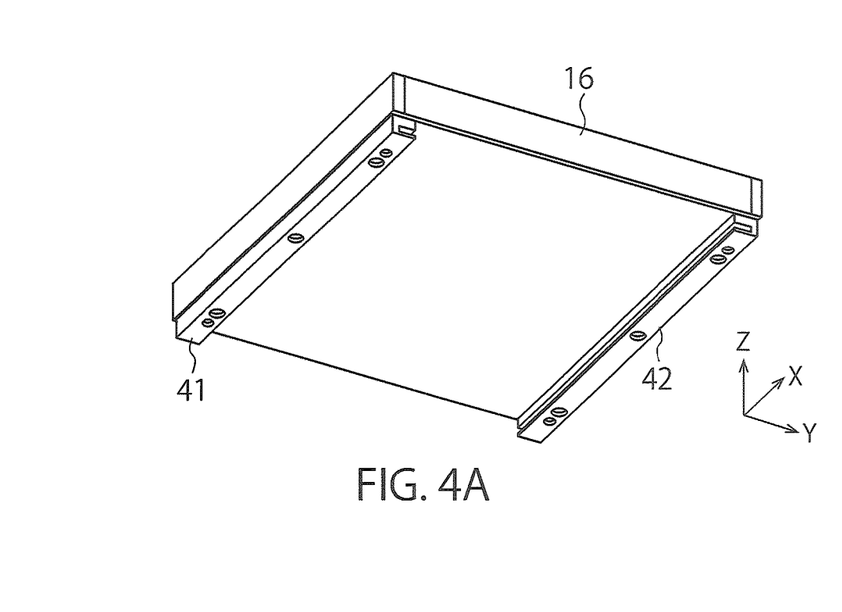
FIG. 4A is a perspective view of the attaching/detaching mechanism as viewed from a front surface of an X-ray detector.
Figure 4B:
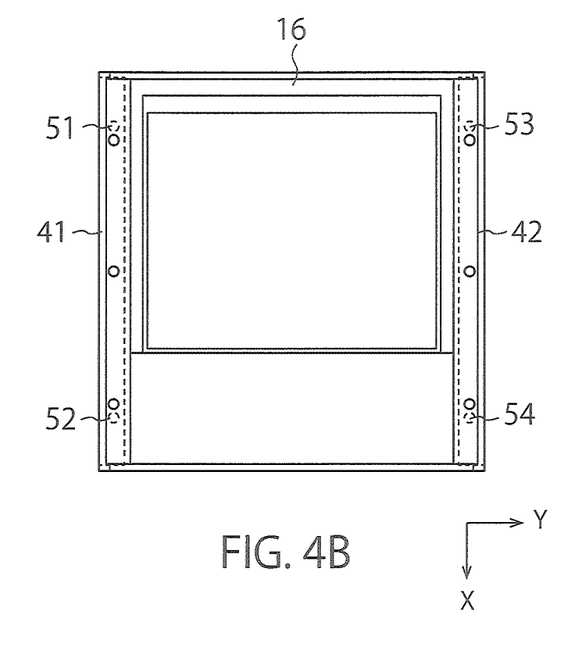
FIG. 4B is a plan view of the attaching/detaching mechanism as viewed from a back surface the X-ray detector.
Figure 4C:
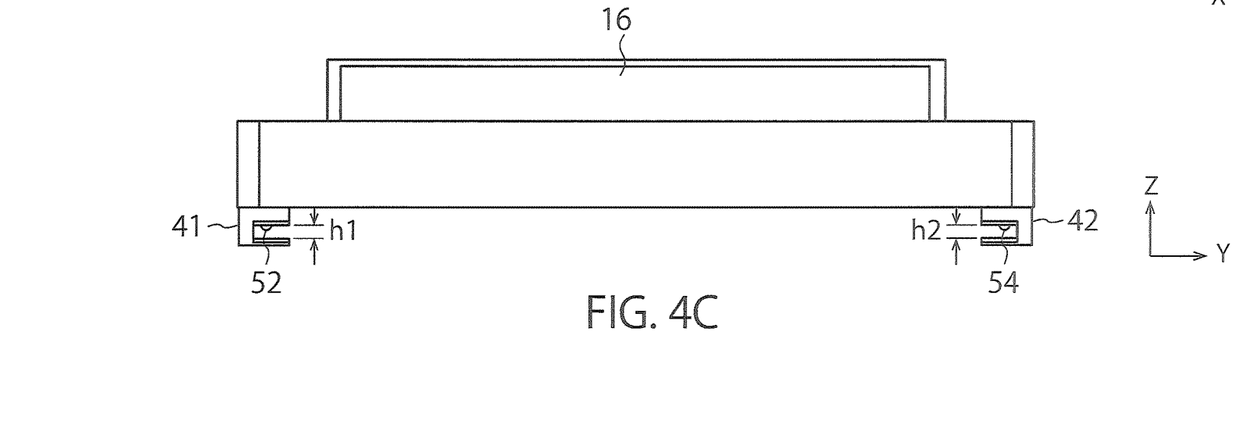
FIG. 4C is a side view of the attaching/detaching mechanism.

FIG. 4A is a perspective view of the attaching/detaching mechanism as viewed from a front surface (a surface opposed to the grid 17) side of the X-ray detector 16. FIG. 4B is a plan view of the attaching/detaching mechanism as viewed from a back surface side of the X-ray detector 16. FIG. 4C is a side view of the attaching/detaching mechanism.

As illustrated in FIGS. 4A to 4C, a first guide 41 and a second guide 42 are fixed onto the front surface of the X-ray detector 16, that is, an X-ray incident surface to be opposed to each other in the Y-direction. The first guide 41 and the second guide 42 each have a square U-shaped cross section. In a case where the thickness t1 of the first rail 31 is different from the thickness t2 of the second rail 32 in order to prevent misattachment of the grid 17, a height h1 of the first guide 41 into which the first rail 31 is inserted is different from a height h2 of the second guide 42 into which the second rail 32 is inserted. For example, in a case where the thickness t1 of the first rail 31 is thinner than the thickness t2 of the second rail 32, the height h1 of the first guide 41 is lower than the height h2 of the second guide 42.

Further, a ball plunger 51 and a ball plunger 52 are provided in an upper portion of the first guide 41. The ball plunger 51 and the ball plunger 52 are an example of a first support. Further, a ball plunger 53 and a ball plunger 54 are provided in an upper portion of the second guide 42. The ball plunger 53 is an example of a third support, and the ball plunger 54 is an example of a second support. Each support is not limited to a ball plunger and may be an elastic support member such as a leaf spring.

As illustrated in FIG. 4B, a distance between the ball plunger 51 and the ball plunger 52 is equal to a distance between the ball plunger 53 and the ball plunger 54. That is, the ball plungers 51 to 54 are arranged symmetrically with respect to the X-direction and the Y-direction. As for the arrangement of the ball plungers 51 to 54, it suffices that the ball plungers 53 and 54 are located on the same line in the X-direction in the present invention, and there is no other restriction.

Figure 5A:
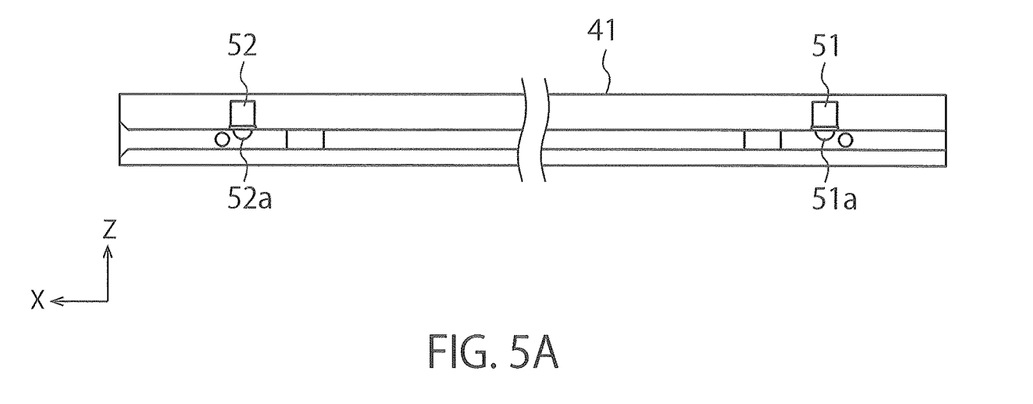
FIG. 5A is a diagram illustrating inside of a first guide.
Figure 5B:
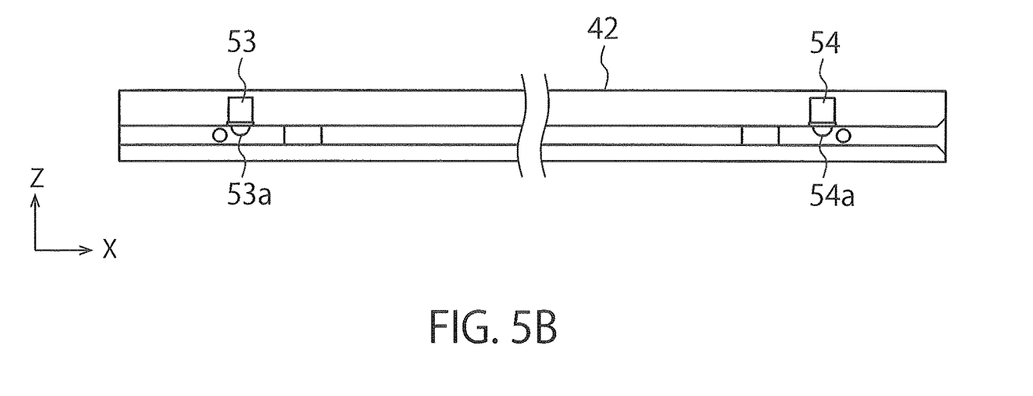
FIG. 5B is a diagram illustrating inside of a second guide.

FIG. 5A is a diagram illustrating inside of the first guide 41, and FIG. 5B is a diagram illustrating inside of the second guide 42. As illustrated in FIGS. 5A and 5B, the ball plungers 51 to 54 have spherical tips 51*a* to 54*a*, respectively. The tips 51a to 54a are each connected to an elastic member (not illustrated), for example, a spring incorporated in the main body. The tips 51a to 54a are each displaced in the Z-direction by an elastic force of this elastic member.

Figure 6:
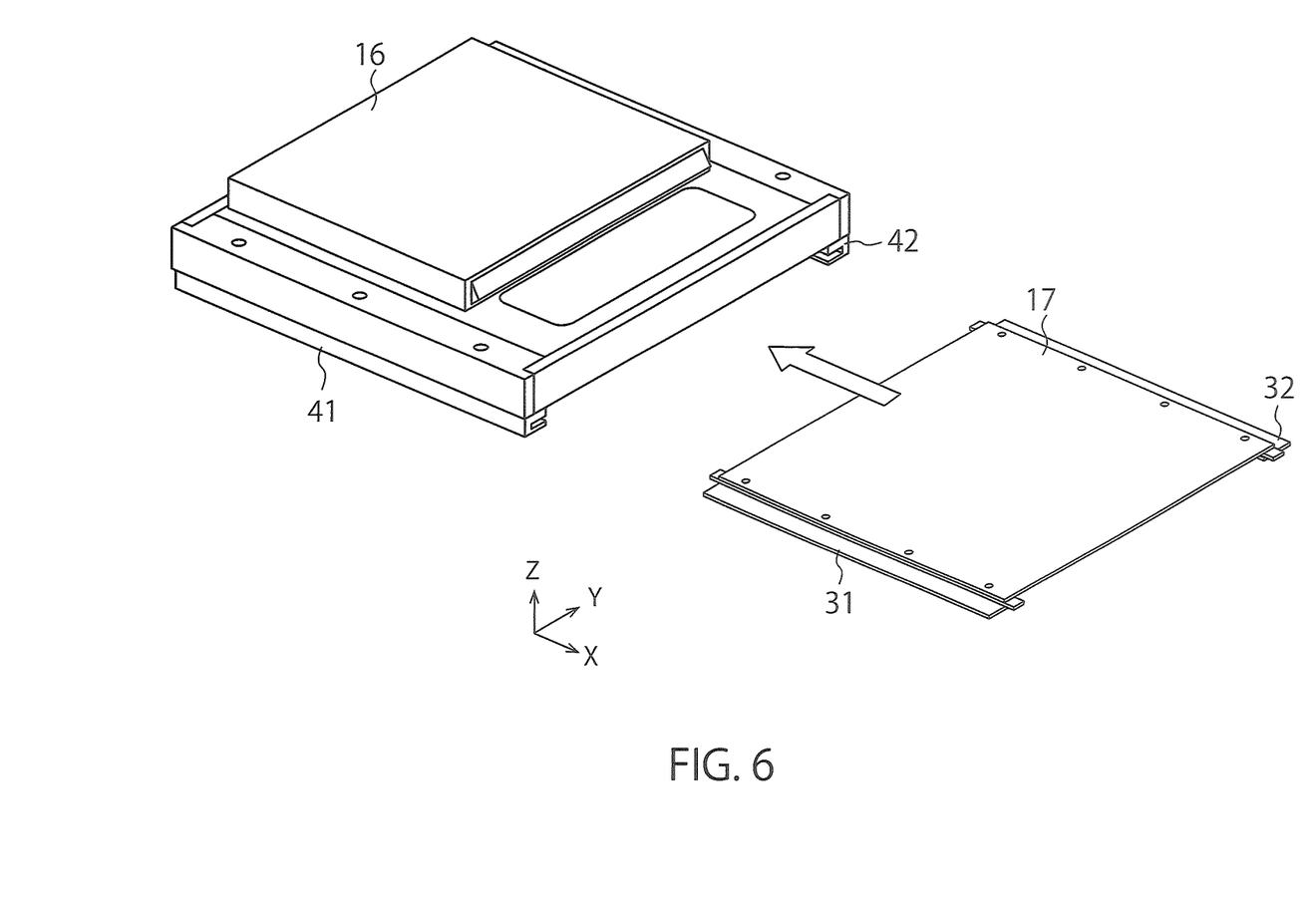
FIG. 6 is a perspective view illustrating a state before the grid is attached to the X-ray detector.
Figure 7:
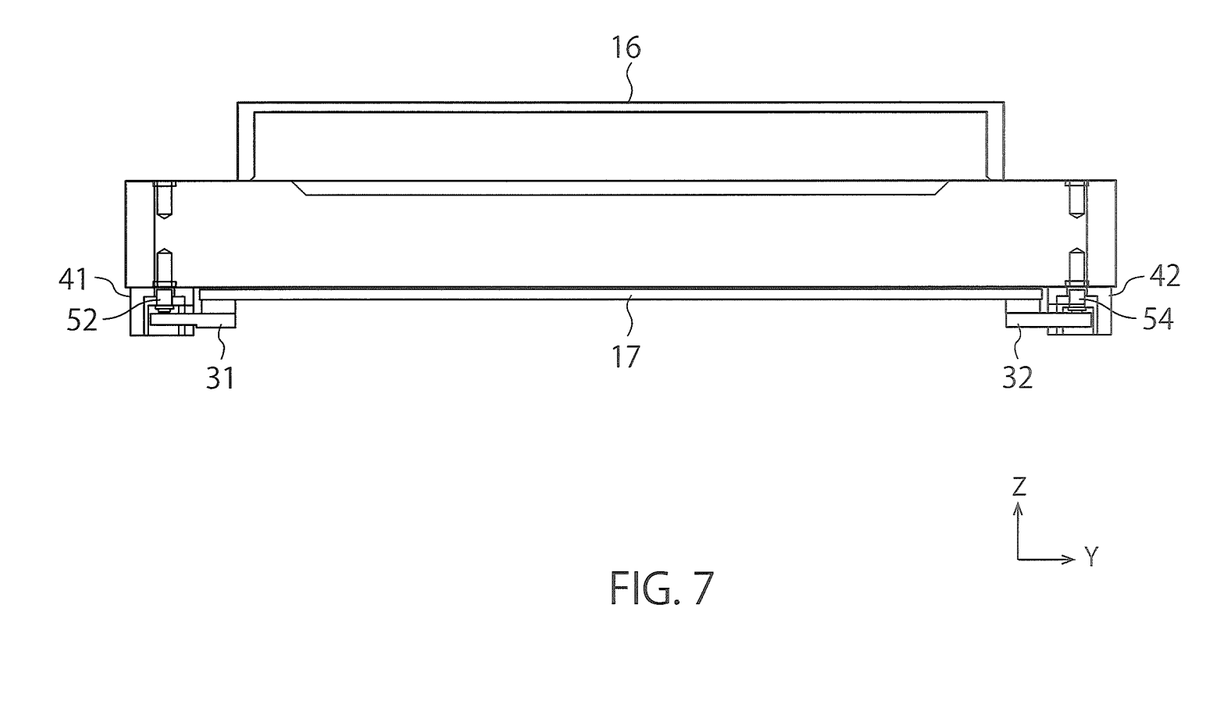
FIG. 7 is a side view illustrating a state after the grid has been attached to the X-ray detector.

Next, a procedure of attaching the grid 17 to the X-ray detector 16 by using the above-described attaching/detaching mechanism is described with reference to FIGS. 6 and 7. FIG. 6 is a perspective view illustrating a state before the grid 17 is attached to the X-ray detector 16. FIG. 7 is a side view illustrating a state after the grid 17 has been attached to the X-ray detector 16.

As illustrated in FIG. 6, the position of the grid 17 is adjusted in such a manner that the first rail 31 is inserted into the first guide 41 and the second rail 32 is inserted into the second guide 42. When the first rail 31 and the second rail 32 are inserted into the first guide 41 and the second guide 42, respectively, the ball plunger 52 presses a planar region in a top surface of the first rail 31 and the ball plunger 54 presses the groove 133 formed in a top surface of the second rail 32. At this stage, movement in the X-direction of the grid 17 is not restricted. Therefore, when the grid 17 is kept sliding toward the back of the X-ray detector 16, the first rail 31 travels along the planar region of the first guide 41 and the second rail 32 travels along the groove 133 of the second guide 42.

Thereafter, when the ball plunger 54 fits into the centering hole 134 of the second rail 32 as illustrated in FIG. 7, the grid 17 is attached to the X-ray detector 16. At this time, the ball plunger 51 and the ball plunger 52 press the planar region in the top surface of the first rail 31, thereby movement in the Z-direction of the grid 17 is restricted. Further, the ball plunger 53 presses the groove 133 formed in the top surface of the second rail 32, thereby movement in the Y-direction and the Z-direction of the grid 17 is restricted. Further, the ball plunger 54 presses the centering hole 134 formed in the top surface of the second rail 32, thereby movement in the X-direction, the Y-direction, and the Z-direction of the grid 17 is restricted. When the grid 17 is pulled out to the front side by a stronger force than a pressing force of each ball plunger, the grid 17 can be detached from the X-ray detector 16.

Figure 8:
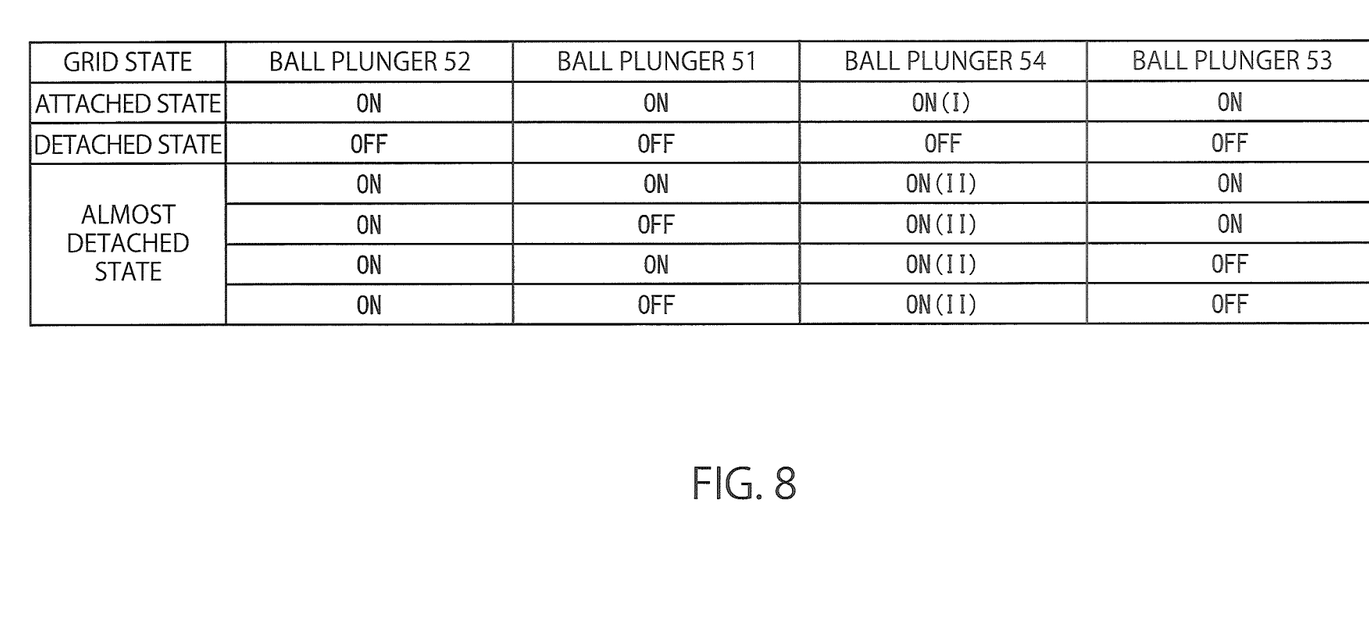
FIG. 8 is a table representing a relation between states of attachment of the grid and states of each ball plunger.

Next, a method of determining the state of attachment of the grid 17 to the X-ray detector 16 is described with reference to FIG. 8. FIG. 8 is a table that representing a relation between states of attachment of the grid 17 and states of each ball plunger.

In the table in FIG. 8, the states of attachment of the grid 17 are defined as "attached state", "detached state", and "almost detached state". The "attached state" refers to a state where the grid 17 has been attached to the X-ray detector 16. The "detached state" refers to a state where the grid 17 has been detached from the X-ray detector 16. The "almost detached state" refers to a state where the grid 17 is about to be detached from the X-ray detector 16, that is, a state where the grid 17 is not fixed to the X-ray detector 16.

The state of each ball plunger is defined as "ON", "ON(I)", "ON(II)", and "OFF". "ON" refers to a state where either one of the ball plungers 51 to 54 is pressing the corresponding first rail 31 or second rail 32. "ON(I)" refers to a state where the ball plunger 54 is pressing the centering hole 134. "ON(II)" refers to a state where the ball plunger 54 is pressing the groove 133. "OFF" refers to a state where either one of the ball plungers 51 to 54 is not pressing the corresponding first rail 31 or second rail 32.

According to the table in FIG. 8, it is possible to ascertain the above three states of the grid 17 by detecting the state of pressing by the ball plunger 54. As described above, the ball plunger 54 has the spherical tip 54a that is displaceable in the Z-direction. The position of the tip 54a changes in accordance with the state of pressing by the ball plunger 54. Therefore, the determination function 211 of the processing circuitry 21 can determine the state of attachment of the grid 17 based on the position of the tip 54a detected by, for example, a position sensor. The determination result is displayed on the display 19. Accordingly, it is possible to perform X-ray examination after checking the state of attachment of the grid 17.

Means for determining the state of attachment of the grid 17 is not limited to the position of the tip 54a. The determination function 211 may determine the state of attachment of the grid 17 based on a pressing force of the ball plunger 54 or a detection result of an electric resistance corresponding to that pressing force, for example. In any case, it is possible to determine the state of attachment of the grid 17 by using the state of pressing by the ball plunger 54 that fits into the centering hole 134 in the "attached state".

In particular, the centering hole 134 and the ball plunger 54 corresponding thereto are provided on the front side (the side having larger X-coordinates in FIG. 6) in a direction of insertion of the grid 17 (an X-axis negative direction in FIG. 6). For example, the ball plunger 54 corresponding to the centering hole 134 is located on the front side in the direction of insertion of the grid 17, with respect to the ball plunger 53 not corresponding to the centering hole 134. Accordingly, from an initial stage of insertion of the grid 17, it is possible to determine that the grid state is an "almost detached state". In the present embodiment, the determination function 211 determines the state of attachment of the grid 17 to the X-ray detector 16 based on the state of the ball plunger 54. However, the determination method is not limited thereto. The determination function 211 may make determination based on the state of at least one of the ball plungers 51 to 53.

According to the present embodiment described above, the ball plunger 51 and the ball plunger 52 restrict movement in one direction of the grid 17 on the side close to the first rail 31 provided in the grid 17. Meanwhile, on the side close to the second rail 32, the ball plunger 53 restricts movement in two directions of the grid 17 and the ball plunger 54 restricts movement in three directions of the grid 17. In the present embodiment, the number of directions in which movement of the grid 17 is restricted is adjusted and the grid 17 is fixed to the X-ray detector 16 in this manner. Therefore, high dimension accuracy is not required for a gap between the first rail 31 and the first guide 41 and a gap between the second rail 32 and the second guide 42 in order to fix the grid 17. Accordingly, it is possible to attach and detach the grid 17 to and from the X-ray detector 16 without being constrained by high processing accuracy.

Further, in a case where the first rail 31 and the second rail 32 are different from each other in the thickness and the first guide 41 and the second guide 42 are different from each other in the height, insertion of the first rail 31 into the second guide 42 and insertion of the second rail 32 into the first guide 41 cannot be made even if such insertion is attempted. Accordingly, it is possible to prevent misattachment of the grid 17.

Second Embodiment

A second embodiment is described. In the present embodiment, an attaching/detaching mechanism for the grid 17 is different from that in the first embodiment. The attaching/detaching mechanism for the grid 17 according to the present embodiment is described below with reference to FIGS. 9 to 11.

Figure 9:
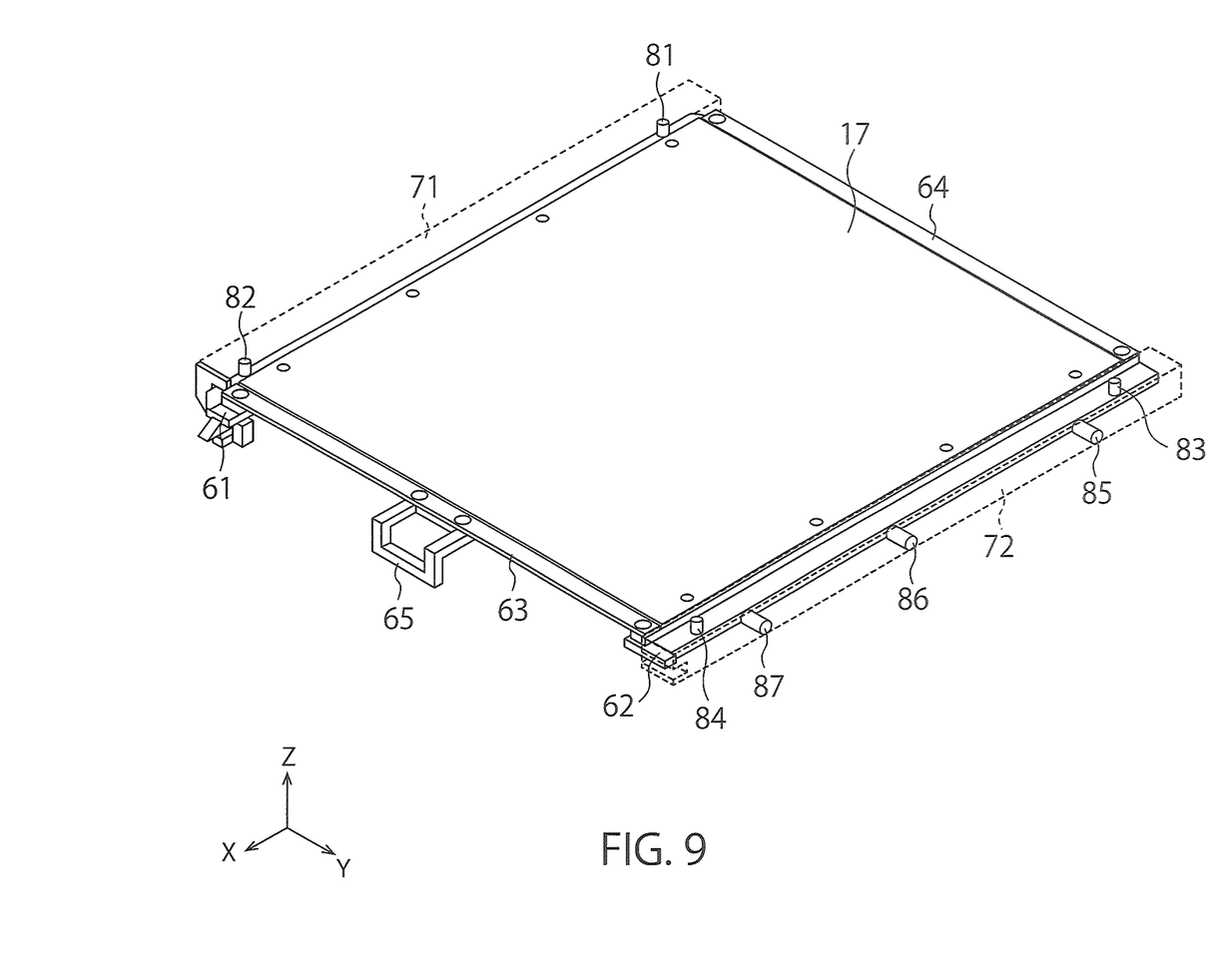
FIG. 9 is a perspective view of an attaching/detaching mechanism for a grid according to a second embodiment.
Figure 10A:
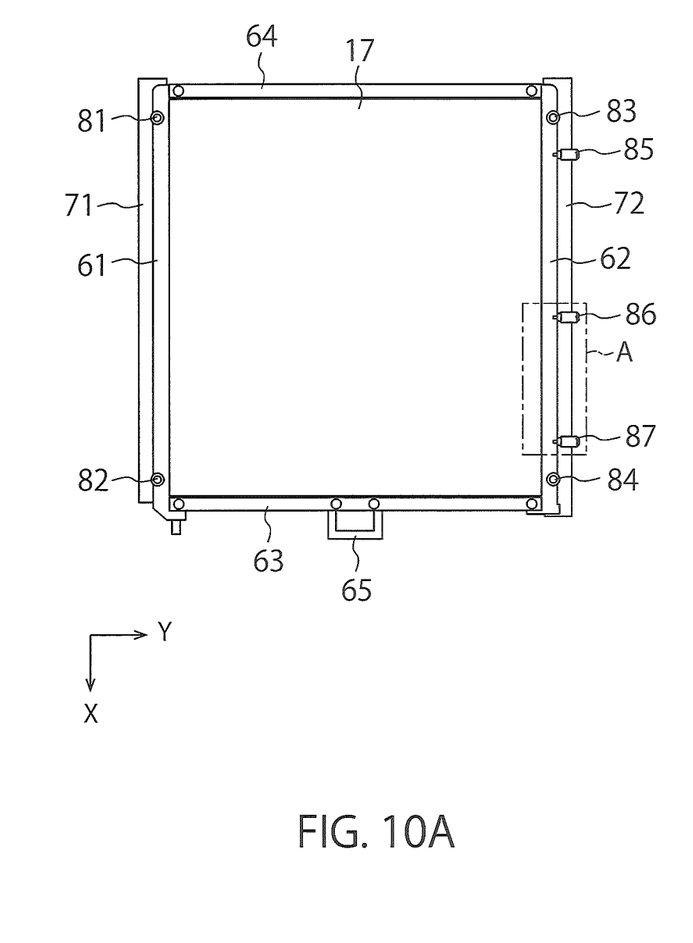
FIG. 10A is a plan view of the attaching/detaching mechanism for the grid according to the second embodiment.
Figure 10B:
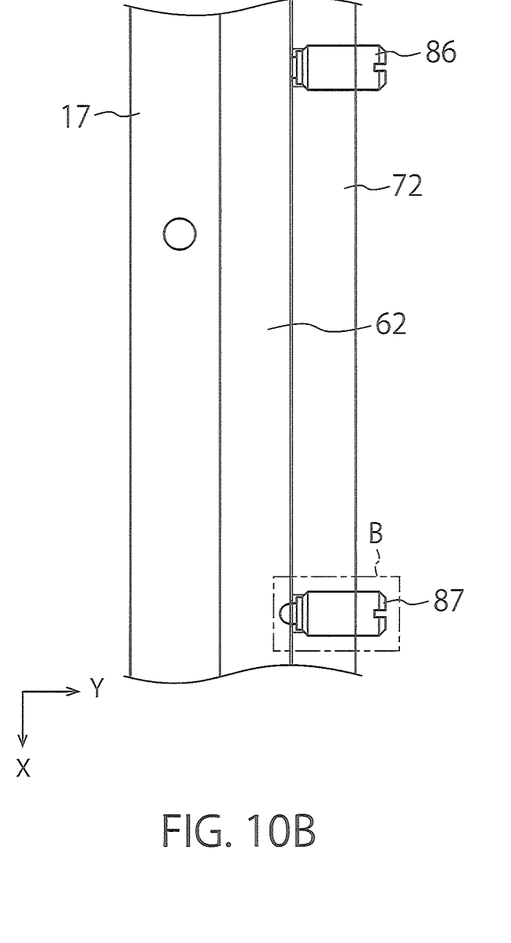
FIG. 10B is an enlarged view of a region A in FIG. 10A.
Figure 11:
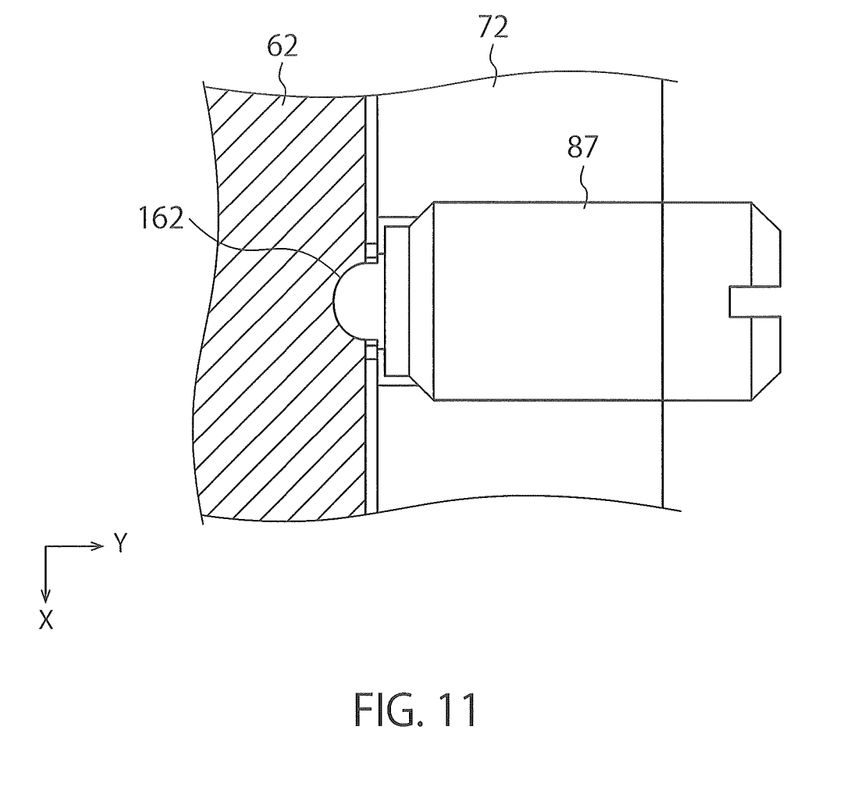
FIG. 11 is an enlarged view of a region B in FIG. 10B.

FIG. 9 is a perspective view of an attaching/detaching mechanism for the grid 17 according to the second embodiment. FIG. 10A is a plan view of the attaching/detaching mechanism for the grid 17 according to the second embodiment, and FIG. 10B is an enlarged view of a region A in FIG. 10A. FIG. 11 is an enlarged view of a region B in FIG. 10B. FIGS. 9 to 11 are diagrams perspectively projecting inside of a first guide 71 and a second guide 72 for better understanding of the structure of the attaching/detaching mechanism.

As illustrated in FIG. 9, a first rail 61 is fixed to one end of the grid 17 which extends in the X-direction, and a second rail 62 is fixed to the other end opposed to the one end in the Y-direction. In other words, the first rail 61 and the second rail 62 are fixed to both end portions of the grid 17 to be opposed to each other in the Y-direction.

The first rail 61 and the second rail 62 are flat plate members. A top surface of each rail is entirely a planar region. That is, the groove 133 and the centering hole 134 described in the first embodiment are not formed in the top surface of the second rail 62. Meanwhile, a V-shaped cutout (notch) 162 is formed in a portion of a side surface of the second rail 62, as illustrated in FIG. 11. A ball plunger 87 fits into the cutout 162. The cutout 162 is another example of a concave portion.

Further, the first rail 61 and the second rail 62 are coupled to each other by a fixing plate 63 and a fixing plate 64, as illustrated in FIG. 9. The fixing plate 63 is arranged on the front side in the grid 17 in the X-direction. Meanwhile, the fixing plate 64 is arranged on the back side in the grid 17 in the X-direction. A handle 65 is provided at the center of the fixing plate 63. This handle 65 makes it easier to attach and detach the grid 17.

The first rail 61 is inserted into the first guide 71 and the second rail 62 is inserted into the second rail 72. The first guide 71 and the second guide 72 each have a square U-shaped cross section as in the first embodiment, and are fixed to a front surface of the X-ray detector 16 to be opposed to each other in the Y-direction.

A ball plunger 81 and a ball plunger 82 are provided in an upper portion of the first guide 71, and a ball plunger 83 and a ball plunger 84 are provided in an upper portion of the second guide 72. The ball plungers 81 to 84 are another example of the first support. The distance between the ball plunger 81 and the ball plunger 82 is equal to the distance between the ball plunger 83 and the ball plunger 84. That is, the ball plungers 81 to 84 are arranged symmetrically with respect to the X-direction and the Y-direction. Also regarding the arrangement of the ball plungers 81 to 84, it suffices that the ball plungers 83 and 84 are located on the same line in the X-direction in the present invention, and there is no other restriction.

Further, a ball plunger 85 and a ball plunger 86 are provided in a side portion of the second guide 72. The ball plunger 85 and the ball plunger 86 are another example of the third support. In the present embodiment, the ball plunger 86 is provided on the front side in the X-direction with respect to the ball plunger 85.

In the side portion of the second guide 72, the ball plunger 87 is provided on the front side in the X-direction with respect to the ball plunger 86. The ball plunger 87 is another example of the second support. In the present embodiment, the ball plungers 85 to 87 are arranged at regular intervals. However, the ball plungers 85 to 87 may not be arranged at regular intervals in the present invention.

Each of the ball plungers 81 to 87 described above also has a spherical tip and is displaced by an elastic force of an elastic member, for example, a spring incorporated in the main body, as in the first embodiment.

Next, a procedure of attaching the grid 17 to the X-ray detector 16 by using the above-described attaching/detaching mechanism is described.

Also in the present embodiment, the position of the grid 17 is adjusted in such a manner that the first rail 61 is inserted into the first guide 71 and the second rail 62 is inserted into the second guide 72, as in the first embodiment. When the first rail 61 and the second rail 62 are inserted into the first guide 71 and the second guide 72, respectively, the ball plunger 82 presses a planar region in a top surface of the first rail 61 and the ball plunger 84 presses a planar region in a top surface of the second rail 62. At this stage, movement in the X-direction of the grid 17 is not restricted. Therefore, when the grid 17 is kept sliding toward the back of the X-ray detector 16, the first rail 61 travels along the planar region of the first guide 71 and the second rail 62 travels along the planar region of the second guide 72.

Thereafter, when the ball plunger 87 fits into the cutout 162 formed in the side surface of the second rail 62 as illustrated in FIG. 11, the grid 17 is attached to the X-ray detector 16. At this time, the ball plungers 81 to 84 press the planar regions in the respective top surfaces of the first rail 61 and the second rail 62, thereby movement in the Z-direction of the grid 17 is restricted.

Further, the ball plunger 85 and the ball plunger 86 press the planar region in the side surface of the second rail 62, thereby movement in the Y-direction of the grid 17 is restricted. Furthermore, the ball plunger 87 presses the cutout 162 formed in the side surface of the second rail 62, thereby movement in the X-direction and the Y-direction of the grid 17 is restricted. When the grid 17 is pulled out toward the front side using the handle 65 by a stronger force than a pressing force of each ball plunger, the grid 17 can be detached from the X-ray detector 16.

Further, in the present embodiment, a state where the ball plunger 87 presses the second rail 62 is different in accordance with the three states (the attached state, the detached state, and the almost detached state) of the grid 17 described in the first embodiment. Therefore, in the present embodiment, the determination function 211 of the processing circuitry 21 can determine the state of attachment of the grid 17 based on the position of a tip of the ball plunger 87 detected by a position sensor or the like. Further, the determination result can be displayed on the display 19.

According to the present embodiment described above, the number of directions in which movement of the grid 17 is restricted by ball plungers is adjusted and the grid 17 is fixed to the X-ray detector 16, as in the first embodiment. Therefore, it is possible to attach and detach the grid 17 to and from the X-ray detector 16 without being constrained by high processing accuracy. In particular, in the second rail 62, it is unnecessary to process the groove 133 and the centering hole 134 formed in the second rail 32 of the first embodiment. Accordingly, the second rail 62 can be processed easily.

Further, in the first embodiment, all ball plungers are provided to be displaceable in the Z-direction. Therefore, when the size of each ball plunger is increased in order to ensure a sufficient fixing force of the grid 17, it is necessary to make the first guide 41 and the second guide 42 that accommodate the ball plungers high. In this case, the distance between the grid 17 and the X-ray detector 16 becomes long, and therefore the image quality of an X-ray image may become insufficient.

Meanwhile, in the present embodiment, one or more of the ball plungers is provided to be displaceable in the Y-direction. Therefore, even when the size of each of the ball plungers 85 to 87 is made larger than those of the ball plungers 81 to 84 that are displaced in the Z-direction in order to ensure a sufficient fixing force of the grid 17, the heights of the first guide 71 and the second guide 72 can be suppressed. As a result, the distance between the grid 17 and the X-ray detector 16 can be set to the bare minimum, and therefore the image quality of an X-ray image can be made sufficient.

Furthermore, in the present embodiment, the ball plungers 85 to 87 are provided in the second guide 72 only, and are not provided in the first guide 71. In a case where the ball plungers 85 to 87 are provided in the first guide 71 and the second guide 72, the grid 17 is pressed not only from one end in the Y-direction but also from the other end, which requires balance adjustment of pressing force. Failure in this balance adjustment may cause unstable attachment of the grid 17. However, in the present embodiment, the ball plungers 85 to 87 perform pressing from the second guide 72 side toward the first guide 71 unidirectionally as described above. Therefore, pressing-force adjustment is not required. Accordingly, attachment of the grid 17 becomes stable.

Also in the present embodiment, in order to prevent misattachment of the grid 17, the thickness of the first rail 61 may be different from the thickness of the second rail 62 and the height of the first guide 71 may be different from the height of the second guide 72. In this case, when the second rail 62 is made thicker than the first rail 61, the area of contact with the ball plungers 85 to 87 is increased in the second rail 62. As a result, the grid 17 can be fixed to the X-ray detector 16 by a larger pressing force, so that fixing of the grid 17 becomes more stable.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
an X-ray generator configured to generate X-rays;
a grid configured to remove scattered rays from X-rays emitted from the X-ray generator;
an X-ray detector configured to detect X-rays that have passed through the grid;
a first support configured to support the grid by pressing the grid; and
a second support configured to support the grid by pressing the grid, wherein
a number of directions in which the first support restricts movement of the grid is different from a number of directions in which the second support restricts movement of the grid,
the first support and the second support are arranged on at least one of two opposite sides of the grid,
directions in which movement of the grid is restricted include a first direction perpendicular to the grid, a second direction that is a direction in which the grid is attached and detached, and a third direction orthogonal to the first direction and the second direction, and
the apparatus further includes a first rail and a second rail provided in the grid to be opposed to each other, and a first guide and a second guide provided in the X-ray detector to be opposed to each other and to be insertable into the first rail and the second rail, respectively, wherein the second rail has a concave portion, and the second support fits into the concave portion to restrict movement of the grid.

2. The apparatus of claim 1, wherein a direction in which the first support restricts movement of the grid is the first direction.

3. The apparatus of claim 1, wherein directions in which the second support restricts movement of the grid are the first direction, the second direction, and the third direction, or the second direction and the third direction.

4. The apparatus of claim 1, wherein a thickness of the first rail is different from a thickness of the second rail, and
a height of the first guide to which the first rail is inserted is different from a height of the second guide to which the second rail is inserted.

5. The apparatus of claim 1, further comprising a third support provided in the second guide at a position away from the second support, wherein
a number of directions in which the third support restricts movement of the grid is different from the number of directions in which the second support restricts movement of the grid.

6. The apparatus of claim 5, wherein the first support presses a top surface of the first rail and a top surface of the second rail, and the second support and the third support press a side surface of the second rail, when the grid is attached to the X-ray detector.

7. The apparatus of claim 6, wherein the first support presses planar regions in the respective top surfaces of the first rail and the second rail, the second support presses a concave portion which is formed in the side surface, and the third support presses a planar region in the side surface.

8. The apparatus of claim 7, wherein the concave portion is a V-shaped cutout.

9. The apparatus of claim 6, further comprising processing circuitry configured to determine a state of attachment of the grid to the X-ray detector based on a state of at least one of the first support, the second support, and the third support.

10. The apparatus of claim 9, wherein the second support is located on a front side with respect to the third support in a direction of insertion of the grid, and
the processing circuitry is further configured to determine the state of the attachment based on a state of the second support.

11. The apparatus of claim 5, wherein the first support presses a top surface of the first rail, and the second support and the third support press a top surface of the second rail, when the grid is attached to the X-ray detector.

12. The apparatus of claim 11, wherein the first support presses a planar region in the top surface of the first rail, the second support presses the concave portion which is formed in the top surface of the second rail, and the third support presses a groove extending in the second direction in the top surface of the second rail.

13. The apparatus of claim 12, wherein the concave portion is a hole adjacent to the groove in the second direction.

14. An X-ray diagnostic apparatus, comprising:
an X-ray generator configured to generate X-rays;

a grid configured to remove scattered rays from X-rays emitted from the X-ray generator;

an X-ray detector configured to detect X-rays that have passed through the grid;

a first support configured to support the grid by pressing the grid; and a second support configured to support the grid by pressing the grid, wherein a number of directions in which the first support restricts movement of the grid is different from a number of directions in which the second support restricts movement of the grid, wherein the apparatus further comprises:

a first rail and a second rail provided in the grid to be opposed to each other; and a first guide and a second guide provided in the X-ray detector to be opposed to each other and to be insertable into the first rail and the second rail, respectively, wherein the second rail has a concave portion, and the second support fits into the concave portion to restrict movement of the grid.

\* \* \* \* \*